United States Patent
Chuang et al.

(10) Patent No.: US 11,071,468 B2
(45) Date of Patent: Jul. 27, 2021

(54) DETECTING APPARATUS AND DETECTING METHOD FOR PHYSIOLOGICAL INFORMATION

(71) Applicant: INDUSTRIAL TECHNOLOGY RESEARCH INSTITUTE, Hsinchu (TW)

(72) Inventors: Chun-Te Chuang, Kaohsiung (TW); Tai-Jie Yun, Taichung (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 676 days.

(21) Appl. No.: 15/674,330

(22) Filed: Aug. 10, 2017

(65) Prior Publication Data
US 2018/0192899 A1 Jul. 12, 2018

(30) Foreign Application Priority Data
Jan. 9, 2017 (TW) .................................. 106100618

(51) Int. Cl.
*A61B 5/024* (2006.01)
*A61B 5/00* (2006.01)

(52) U.S. Cl.
CPC ........ *A61B 5/02416* (2013.01); *A61B 5/6826* (2013.01); *A61B 5/7221* (2013.01);
(Continued)

(58) Field of Classification Search
CPC . A61B 5/02416; A61B 5/7221; A61B 5/7207; A61B 5/7275; A61B 5/746
See application file for complete search history.

(56) References Cited

U.S. PATENT DOCUMENTS 4,819,646 A * 4/1989 Cheung .............. A61B 5/14551
600/323
7,336,982 B2 2/2008 Yoo
(Continued)

FOREIGN PATENT DOCUMENTS

CN 101198277 A 6/2008
CN 101365378 A 2/2009
(Continued)

OTHER PUBLICATIONS

D. Shao et al., "Noncontact Monitoring of Blood Oxygen Saturation Using Camera and Dual-Wavelength Imaging System," in *IEEE Transactions on Biomedical Engineering*, vol. 63, No. 6, Jun. 2016, pp. 1091-1098.
(Continued)

*Primary Examiner* — Keith M Raymond
*Assistant Examiner* — Milton Truong
(74) *Attorney, Agent, or Firm* — Muncy, Geissler, Olds & Lowe, P.C.

(57) ABSTRACT

A detecting apparatus and a detecting method for physiological information are provided. The detecting apparatus includes a first optical signal provider configured to provide an organism with a first optical signal, a signal receiver configured to receive the first physiological signal, and a processor. The first optical signal, after interacting with the organism, turns into a first physiological signal. The processor is configured to calculate a plurality of physiological information values of the organism according to the first physiological signal; determine whether or not any of the physiological information values is abnormal; and replace the abnormal physiological information value with a physiological information reliable value when there is the abnormal physiological information value.

15 Claims, 10 Drawing Sheets

(52) U.S. Cl.
CPC ............ *A61B 5/7275* (2013.01); *A61B 5/746* (2013.01); *A61B 5/7207* (2013.01)

(56) References Cited

U.S. PATENT DOCUMENTS

| | | | |
|---|---|---|---|
| 7,952,692 | B2 | 5/2011 | Primack et al. |
| 8,007,441 | B2 | 8/2011 | Baker, Jr. |
| 8,092,379 | B2 | 1/2012 | Baker, Jr. |
| 8,761,852 | B2 | 6/2014 | Parthasarathy et al. |
| 8,818,476 | B2 | 8/2014 | Besko |
| 9,072,474 | B2 | 7/2015 | Al-Ali et al. |
| 9,149,216 | B2 | 10/2015 | Eisen et al. |
| 9,211,090 | B2 | 12/2015 | Baker, Jr. |
| 9,307,917 | B2 | 4/2016 | Hong et al. |
| 9,314,197 | B2 | 4/2016 | Eisen et al. |
| 9,370,326 | B2 | 6/2016 | McHale et al. |
| 9,375,185 | B2 | 6/2016 | Ali et al. |
| 2008/0194932 | A1* | 8/2008 | Ayers .................. A61B 5/0205 600/324 |
| 2009/0326353 | A1* | 12/2009 | Watson .............. A61B 5/14551 600/330 |
| 2010/0292589 | A1 | 11/2010 | Goodman |
| 2011/0124982 | A1* | 5/2011 | Pipke .................. A61B 5/0205 600/301 |
| 2012/0029320 | A1* | 2/2012 | Watson .............. A61B 5/02416 600/301 |
| 2014/0187880 | A1 | 7/2014 | Hsieh et al. |
| 2015/0245794 | A1* | 9/2015 | Al-Ali ................. A61B 5/14552 600/323 |
| 2016/0120444 | A1 | 5/2016 | Hsu et al. |
| 2018/0353718 | A1* | 12/2018 | Gale .................... A61M 16/026 |

FOREIGN PATENT DOCUMENTS

| | | |
|---|---|---|
| CN | 101632588 A | 1/2010 |
| CN | 102499694 A | 6/2012 |
| CN | 103027690 A | 4/2013 |
| CN | 103315728 A | 9/2013 |
| CN | 103767690 A | 5/2014 |
| CN | 103781404 A | 5/2014 |
| CN | 105740627 A | 7/2016 |
| TW | I538660 B | 6/2016 |
| TW | I541004 B | 7/2016 |
| WO | WO2005065540 A1 | 7/2005 |

OTHER PUBLICATIONS

T. Y. Abay and P. A. Kyriacou, "Reflectance Photoplethysmography as Noninvasive Monitoring of Tissue Blood Perfusion," in *IEEE Transactions on Biomedical Engineering*, vol. 62, No. 9, Sep. 2015, pp. 2187-2195.

G. Pang and C. Ma, "A Neo-Reflective Wrist Pulse Oximeter," in *IEEE Access*, vol. 2, No., 2014, pp. 1562-1567.

K. Li and S. Warren, "A Wireless Reflectance Pulse Oximeter With Digital Baseline Control for Unfiltered Photoplethysmograms," in *IEEE Transactions on Biomedical Circuits and Systems*, vol. 6, No. 3, Jun. 2012, pp. 269-278,.

C. G. Scully et al., "Physiological Parameter Monitoring from Optical Recordings with a Mobile Phone," in *IEEE Transactions on Biomedical Engineering*, vol. 59, No. 2, pp. 303-306, Feb. 2012.

Etienne Gayat et al; "Performance Evaluation of a Noninvasive Hemoglobin Monitoring Device"; Annals of Emergency Medicine; vol. 57, No. 4; Apr. 2011; pp. 330-333.

J. Lee et al, "An Autoregressive Model-Based Particle Filtering Algorithms for Extraction of Respiratory Rates as High as 90 Breaths Per Minute From Pulse Oximeter," in IEEE Transactions on Biomedical Engineering, vol. 57, No. 9, pp. 2158-2167, Sep. 2010.

Tavakoli, L. et al, "An Ultra-Low-Power Pulse Oximeter Implemented With an Energy-Efficient Transimpedance Amplifier," in IEEE Transactions on Biomedical Circuits and Systems, vol. 4, No. 1, pp. 27-38, Feb. 2010.

John R. Feiner et al "Dark Skin Decreases the Accuracy of Pulse Oximeters at Low Oxygen Saturation: The Effects of Oximeter Probe Type and Gender"; International Anesethesia Research Society; vol. 105, No. 6, Dec. 2007, pp. 18-23.

Office Action dated May 18, 2020 in corresponding Chinese Application No. 201710104501.8.

* cited by examiner

DETECTING APPARATUS AND DETECTING METHOD FOR PHYSIOLOGICAL INFORMATION

CROSS-REFERENCE TO RELATED APPLICATION

This application claims the priority benefit of Taiwan application Ser. No. 106100618, filed on Jan. 9, 2017. The entirety of the above-mentioned patent application is hereby incorporated by reference herein.

TECHNICAL FIELD

The technical field relates to a detecting apparatus and a detecting method for physiological information.

BACKGROUND

A detecting apparatus for physiological information, such as smart bracelet, wristband, headband, headphones, and so on, is gradually developed for wearing on organisms easily, which may last long detecting the physiological information of the organism. However, during the long activity of the organism, slight dislocation may exist between this detecting apparatus and the original detecting position of the organism, thereby leading to distorted measuring physiological information. However, the wearable detecting apparatus for physiological information in the market still displays the distorted physiological value to users, which results in the misjudgments of the physiological status. Also, when organisms move between different environments, the organisms may be affected by the change of different ambient lights, thereby resulting in the distorted measurement signal of the detecting apparatus.

In addition, for long-term usage of the wearable detecting apparatus, portability and battery endurance for the apparatus are important and thus a simplified operation may be performed by the operating system of the apparatus for avoiding excessive power consumption.

SUMMARY

According to an embodiment, a detecting apparatus for physiological information is provided. The detecting apparatus includes a first optical signal provider, a signal receiver and a processor. The first optical signal provider is configured to provide an organism with a first optical signal, wherein the first optical signal after interacting with the organism turns into a first physiological signal. The signal receiver is configured to receive the first physiological signal. The processor is configured to calculate a plurality of physiological information values of the organism according to the first physiological signal; determine whether or not there is an abnormal physiological information value of the physiological information values; and replace the abnormal physiological information value with a physiological information reliable value of normal physiological information values of the plurality of physiological information values when there is the abnormal physiological information value.

According to another embodiment, a detecting method for physiological information is provided. The detecting method includes the following steps. A detecting apparatus having a first optical signal provider, a signal receiver, and a processor is provided; an organism is provided with the first optical signal by the first optical signal provider, wherein the first optical signal after interacting with the organism turns into a first physiological signal; the first physiological signal is received by the signal receiver; a plurality of physiological information values of the organism are calculated by the processor according to the first physiological signal; whether or not there is an abnormal physiological information value of the physiological information values is determined by the processor; and the processor replaces the abnormal physiological information value with a physiological information reliable value of normal physiological information values of the plurality of physiological information values when there is the abnormal physiological information.

The foregoing will become better understood from a careful reading of a detailed description provided herein below with appropriate reference to the accompanying drawings.

DETAILED DESCRIPTION OF DISCLOSED EMBODIMENTS

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Figure 1A:
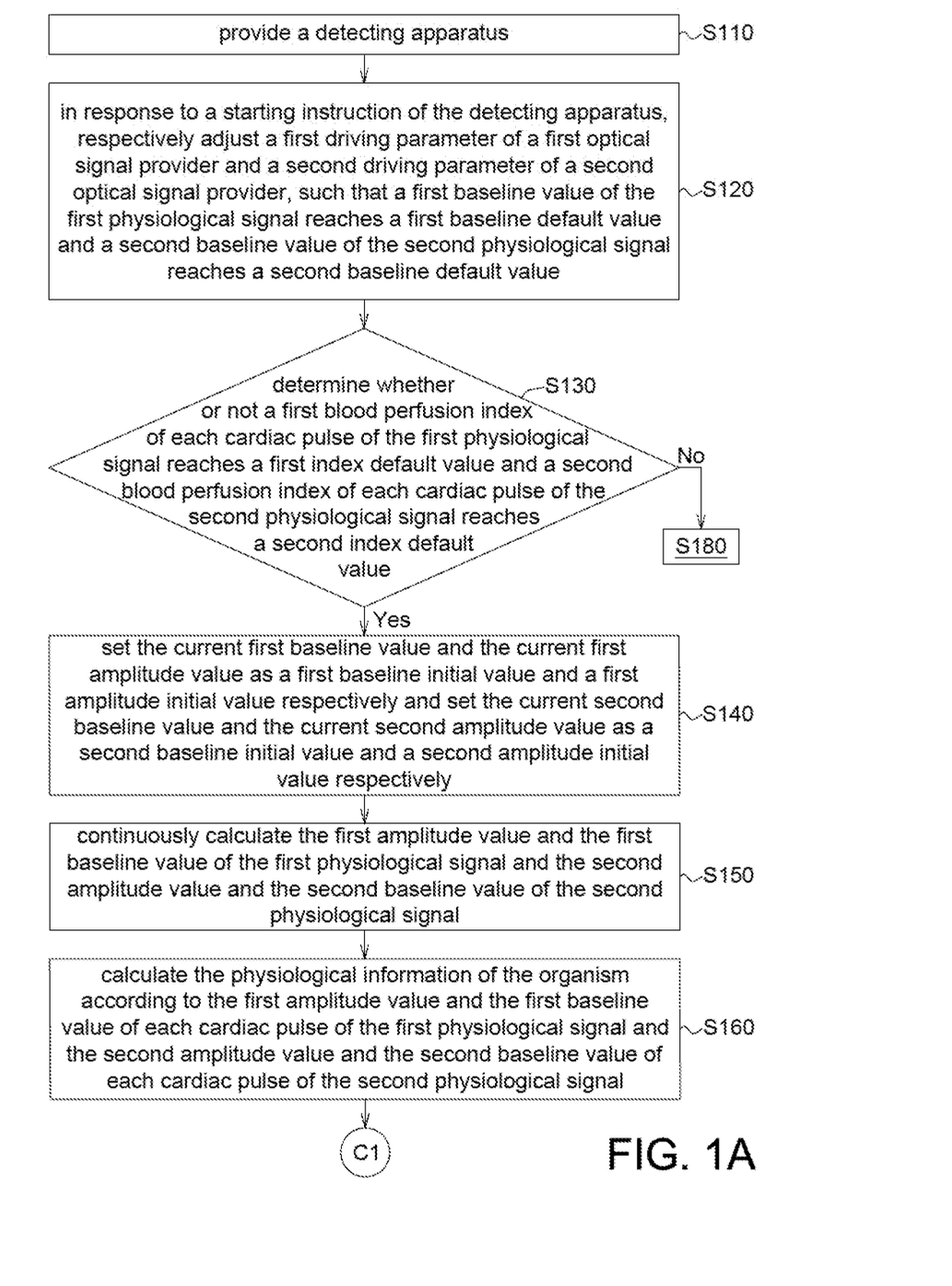
FIGS. 1A and 1B illustrate a flowchart of a detecting method for physiological information according to an embodiment of the present disclosure.
Figure 1B:
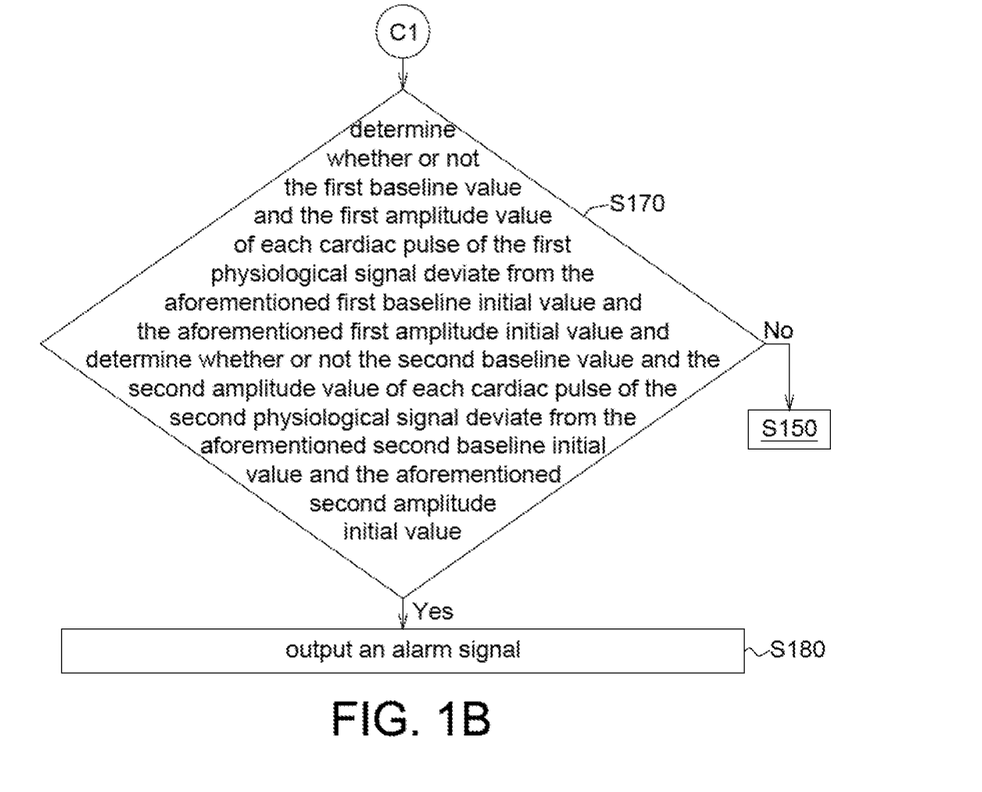
Figure 2:
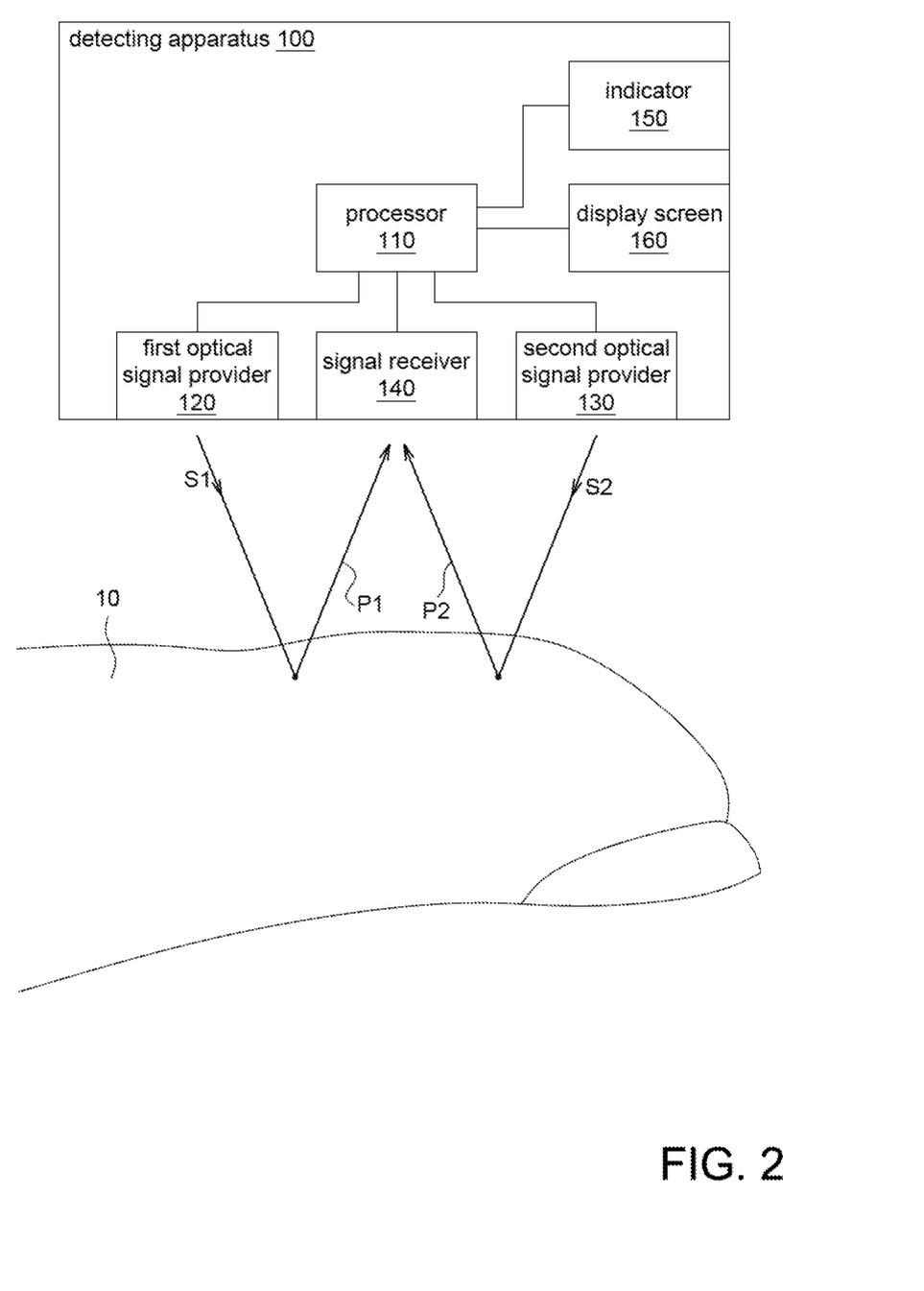
FIG. 2 illustrates a diagram of functional blocks of a detecting apparatus for physiological information according to an embodiment of the present disclosure.

FIGS. 1A and 1B illustrate a flowchart of a detecting method for physiological information according to an embodiment of the present disclosure. FIG. 2 illustrates a block diagram of functional blocks of a detecting apparatus for physiological information 100 according to an embodiment of the present disclosure. Please refer to FIG. 1A, FIG. 1B and FIG. 2.

In the step S110, the detecting apparatus for physiological information 100 is provided. In the embodiment of FIG. 2, the detecting apparatus for physiological information 100 may include a processor 110, a first optical signal provider 120, a second optical signal provider 130, a signal receiver 140, an indicator 150 and a display screen 160. The processor 110 is coupled to the first optical signal provider 120, the second optical signal provider 130 and the signal receiver 140, and is configured to control the first optical signal provider 120 and the second optical signal provider 130 to output optical signals and process and/or analyze the physiological signal received by the signal receiver 140. In an embodiment, the first optical signal provider 120 is, for example, a red light emitter, the second optical signal provider 130 is, for example, an Infrared light emitter, and the signal receiver 140 is, for example, a photo detector (PD); but the scope of the present disclosure is not limited thereto.

In other embodiments, the detecting apparatus for physiological information 100 may not include the second optical signal provider 130, or the indicator 150, or the display screen 160. In other words, the second optical signal provider 130, or the indicator 150, or the display screen 160 may be optional, or may be an external device of the detecting apparatus for physiological information; but the scope of the present disclosure is not limited thereto.

In the step S120, the processor 110, in response to a starting instruction of the detecting apparatus 100, controls the first optical signal provider 120 and the second optical signal provider 130 to provide an organism with the first optical signal S1 and the second optical signal S2, respectively. The starting instruction is generated by the detecting apparatus 100, for example, when the organism 10 initiates a triggering action to the detecting apparatus 100, or the starting instruction is a periodical self-activation of the detecting apparatus 100.

The first optical signal S1 and the second optical signal S2, after interacting with the organism 10 (for example, reflection, transmission, or other optical reactions that may contact the organism 10) turn into a first physiological signal P1 and a second physiological signal P2, respectively, and then the first physiological signal P1 and the second physiological signal P2 are received by the signal receiver 140. The term "interacting with" means that the optical signal S1 or S2 is reflected by or transmitted through the organism 10, but the scope of the present disclosure is not limited thereto. The organism 10 is, for example, any part of a human body or any part of an animal body, such as a finger, a wrist, a limb, and so on. In the step S120, the organism 10 may stay in a stationary state, so that the detecting apparatus 100 may obtain better driving parameters of the optical signal providers.

Figure 3A:
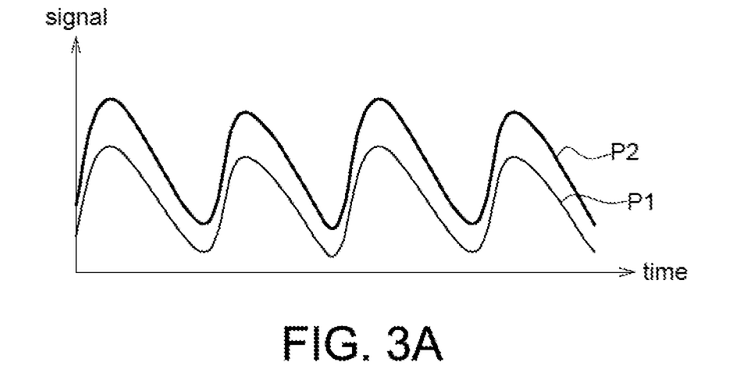
FIGS. 3A-3F illustrate how to process the first physiological signal and the second physiological signal according to an embodiment of the present disclosure.
Figure 3B:
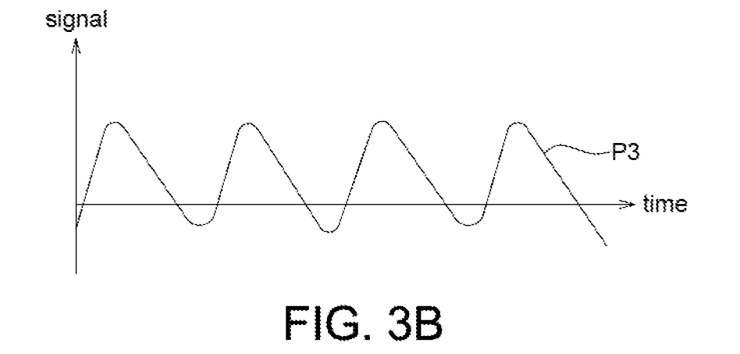
Figure 3C:
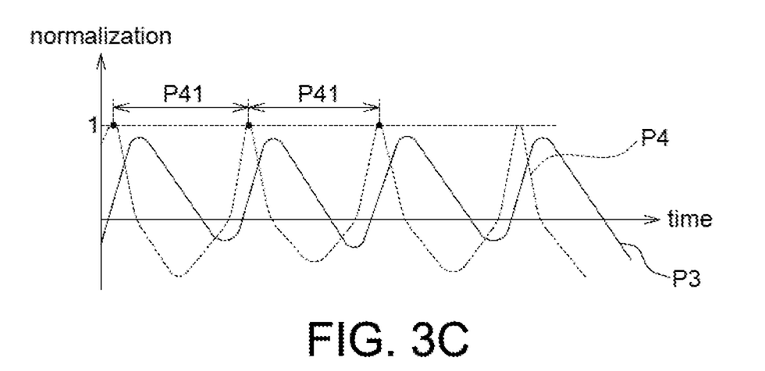
Figure 3D:
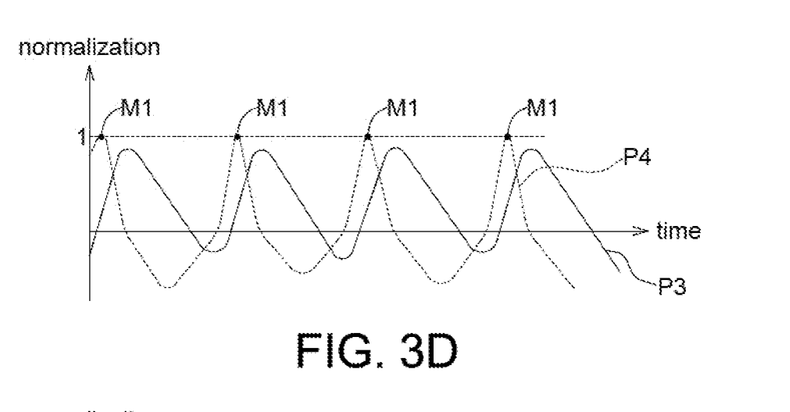
Figure 3E:
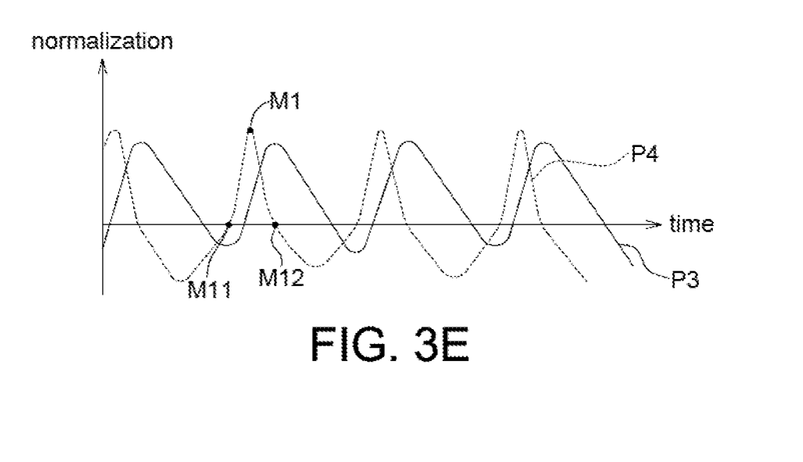
Figure 3F:
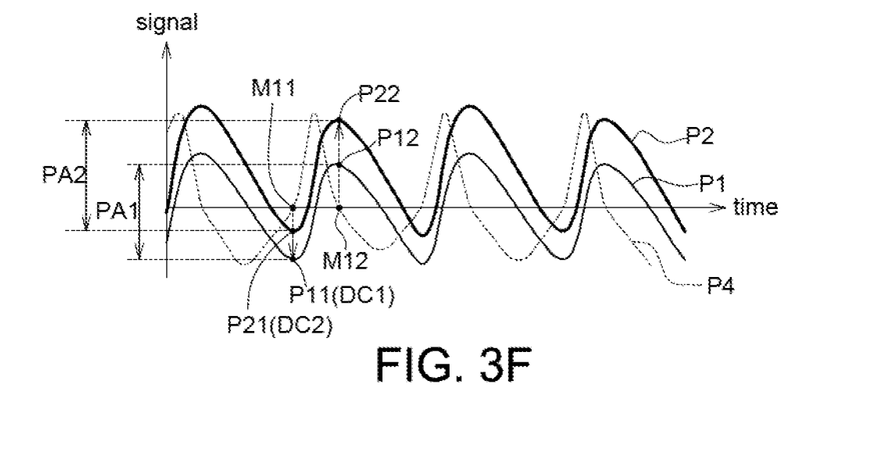

The processor 110 adjusts a first driving parameter of the first optical signal provider 120 and a second driving parameter of the second optical signal provider 130, respectively, such that a first baseline value DC1 (as illustrated in FIG. 3F) of the first physiological signal P1 reaches a first baseline default value, and a second baseline value DC2 (as illustrated in FIG. 3F) of the second physiological signal P2 reaches a second baseline default value. If the first and the second baseline default values cannot be reached, the processor 110 may increase a first driving current for the first optical signal provider 120 and a second driving current for the second optical signal provider 130, respectively, to make the first baseline value DC1 and the second baseline value DC2 reach the first baseline default value and the second baseline default value, respectively. When each of the driving currents has reached an upper limit value, instead of increasing the driving current, a gain of the signal receiver 140 is increased for making the first baseline value DC1 and the second baseline value DC2 reach the first baseline default value and the second baseline default value, respectively. The aforementioned first baseline default value and the second baseline default value are, for example, half of the voltage converted from the physiological signal received by the signal receiver 140. The first optical signal provider 120 and the second optical signal provider 130 may have different or identical driving parameters. That is, the first driving current of the first optical signal provider 120 and the second driving current of the second optical signal provider 130 may be different or identical, and/or a first gain of the first optical signal provider 120 and a second gain of the second optical signal provider 130 may be different or identical.

With the aforementioned light adjustment step, the first optical signal S1 and the second optical signal S2 may be adjusted according to the distribution and the density of the blood vessels in measurement positions or to the ambient light, to increase the accuracy of the detected physiological information.

In the step S130, the processor 110 determines whether or not a first blood perfusion index (PI) of each cardiac pulse of the first physiological signal P1 reaches a first index default value and a second blood perfusion index of each cardiac pulse of the second physiological signal P2 reaches a second index default value. If yes, the processor 110 proceeds to perform step S140; if not, it means that the detecting apparatus 100 is not worn correctly and thus the processor 110 proceeds to perform step S180. In the step S180, the processor 110 controls the indicator 150 or the display screen 160 to output an alarm signal. The organism 10 may put on the detecting apparatus 100 again, and then the processor 110 proceeds to perform the step S120. In addition, the alarm signal may be in the form of light, voice, picture, and vibration, or be other signals capable of informing the organism 10.

The blood perfusion index may be defined as a proportion of the amplitude value of the physiological signal (for example, the first physiological signal P1 and the second physiological signal P2) to the baseline value of the physiological signal (for example, the first physiological signal P1 and the second physiological signal P2). For example, the blood perfusion index of each cardiac pulse of the first physiological signal P1 is a proportion of a first amplitude value PA1 (as illustrated in FIG. 3F) to the first baseline value DC1 (as illustrated in FIG. 3F), and the blood perfusion index of each cardiac pulse of the second physiological signal P2 is a proportion of a second amplitude value PA2 (as illustrated in FIG. 3F) to the second baseline value DC2 (as illustrated in FIG. 3F). In an embodiment, the first index default value and the second index default value are, for example, 3%. However, the first index default value and the second index default value can be less or greater than 3%.

For example, referring to FIGS. 3A-3F, FIGS. 3A-3F illustrate how to process the first physiological signal P1 and the processed second physiological signal P2 according to an embodiment of the present disclosure. Firstly, as illustrated in FIG. 3A, the signal receiver 140 receives the first physiological signal P1 and the second physiological signal P2. The first physiological signal P1 and the second physiological signal P2 of FIG. 3A are the signals obtained within a time interval, for example. The length of the time interval may be, but not limited to 2 seconds. Each of the first physiological signal P1 and the second physiological signal P2 includes a plurality of the cardiac pulses. As illustrated in FIG. 3B, the processor 110 may synthesize the first physiological signal P1 and the second physiological signal P2 to form a synthetic physiological signal P3. As illustrated in FIG. 3C, the processor 110 may perform a bandpass filtering on the synthetic physiological signal P3. Then, the synthetic physiological signal P3 is differentiated once and then normalized by the processor 110, thereby obtaining a differential curve P4. In addition, the processor 110 records a pulse-pulse interval (PPI) P41 of the differential curve P4. As illustrated in FIG. 3D, the processor 110 determines a maximum value of the differential curve P4. Each cardiac pulse has one maximum value M1. Four cardiac pulses are shown in FIG. 3D, and therefore in the PPI, there are four maximum values M1 for the differential curve P4. Then, as illustrated in FIG. 3E, the processor 110 determines two corresponding points M11 and M12 on the differential curve P4, wherein the two corresponding points M11 and M12 are most adjacent to one of the four points having the maximum value M1 of the differential curve P4 and both values of the points M11 and M12 equal or approximate to zero. To simplify the diagram, FIG. 3E illustrates only one group of the corresponding points M11 and M12 for only one of the maximum values M1. As illustrated in FIG. 3F, a first point P11 and a second point P12 may be obtained by finding two points corresponding to the points M11 and M12 in the first physiological signal P1 of FIG. 3A, respectively. The first point P11 corresponding to the point M11 is the wave trough of the first physiological signal P1, and the second point P12 corresponding to the point M12 is the wave crest of the first physiological signal P1. A vertical distance between the first point P11 and the second point P12 is defined as the first amplitude value PA1, and the first point P11 is defined as the first baseline value DC1. Similarly, a first point P21 and a second point P22 may be obtained by finding two points corresponding to the points M11 and M12 in the second physiological signal P2 of FIG. 3A, respectively. The first point P21 corresponding to the point M11 is the wave trough of the second physiological signal P2, and the second point P22 corresponding to the point M12 is the wave crest of the second physiological signal P2. A vertical distance between the first point P21 and the second point P22 is defined as the second amplitude value PA2, and the first point P21 is defined as the second baseline value DC2. After the first baseline value DC1, the first amplitude value PA1, the second baseline value DC2 and the second amplitude value PA2 are obtained, the processor 110 may calculate the first index default value $$\left(\text{for example,} \frac{PA1}{DC1} \times 100\%\right)$$

and the second index default value $$\left(\text{for example,} \frac{PA2}{DC2} \times 100\%\right)$$

according to the first baseline value DC1, the first amplitude value PA1, the second baseline value DC2 and the second amplitude value PA2.

In the step S140, if the first blood perfusion index of each cardiac pulse of the first physiological signal P1 reaches the first index default value and the second blood perfusion index of each cardiac pulse of the second physiological signal P2 reaches the second index default value, the processor 110 records the current first baseline value DC1 and the current first amplitude value PA1 (that is, the first baseline value DC1 and the first amplitude value PA1 which reach the first index default value), sets the current first baseline value DC1 and the current first amplitude value PA1 as a first baseline initial value and a first amplitude initial value, respectively, records the current second baseline value DC2 and the current second amplitude value PA2 (that is, the second baseline value DC2 and the second amplitude value PA2 which reach the second index default value), and sets the current second baseline value DC2 and the current second amplitude value PA2 as a second baseline initial value and a second amplitude initial value, respectively. The first baseline initial value, the first amplitude initial value, the second baseline initial value and the second amplitude initial value may be used for determining whether or not the first amplitude value PA1, the first baseline value DC1, the second amplitude value PA2 and the second baseline value DC2 deviate from the initial values.

In the step S150, the processor 110 continuously calculates the first amplitude value PA1 and the first baseline value DC1 of each cardiac pulse of the first physiological signal P1, and the second amplitude value PA2 and the second baseline value DC2 of each cardiac pulse of the second physiological signal P2 within each time interval according to the operating flows shown in FIGS. 3A-3F.

In the step S160, the processor 110 calculates the physiological information of the organism 10 according to the first amplitude value PA1 and the first baseline value DC1 of each cardiac pulse of the first physiological signal P1, and the second amplitude value PA2 and the second baseline value DC2 of each cardiac pulse of the second physiological signal P2. The physiological information (or physiological parameter) are, for example, pulse rate per minute (hereinafter referred to as "pulse value") and other physiological messages, such as blood oxygen saturation.

In the step S170, the processor 110 determines whether or not the first baseline value DC1 and the first amplitude value PA1 of each cardiac pulse of the first physiological signal P1 deviate from the aforementioned first baseline initial value and the aforementioned first amplitude initial value for a period of time, and determines whether or not the second baseline value DC2 and the second amplitude value PA2 of each cardiac pulse of the second physiological signal P2 deviate from the aforementioned second baseline initial value and the aforementioned second amplitude initial value for a period of time. If yes, the processor 110 proceeds to perform the step S180. In the step S180, an alarm signal is output. If not, the processor 110 goes back to step S150 to continue detecting the physiological information of the organism 10. The aforementioned "a period of time" is, for example, 4 seconds, or shorter or longer than 4 seconds. In addition, the aforementioned "deviate from" means that the first baseline value DC1 deviate from the aforementioned first baseline initial value by a certain percentage, for example, plus or minus 10%. The definition of "deviate from" may also be applied to the first amplitude value PA1, the second baseline value DC2 of the second physiological signal P2 and the second amplitude value PA2 of the second physiological signal P2. The "deviation" may occur when the detecting apparatus 100 is dislocated from the original measurement position of the organism 10.

In the step S180, the processor 110 controls the indicator 150 or the display screen 160 to output the alarm signal. According to the alarm signal, the organism 10 may readjust the detecting apparatus 100 or put on the detecting apparatus 100 again. After the organism 10 readjusts the detecting apparatus 100 or puts on the detecting apparatus 100 again, the processor 110 returns to the step S120.

Figure 4:
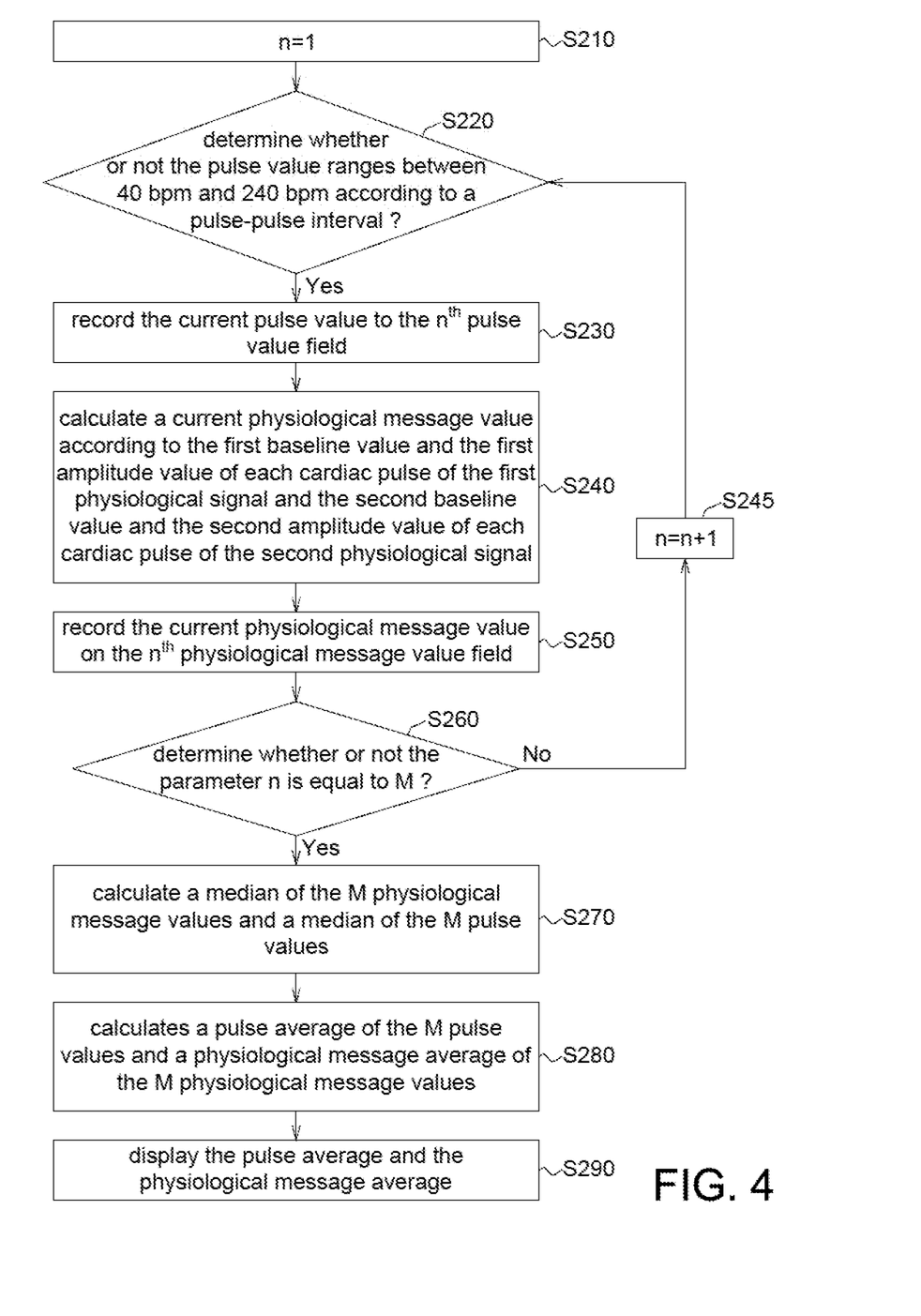
FIG. 4 illustrates a flowchart of the detecting method for physiological information according to another embodiment of the present disclosure.

FIG. 4 illustrates a flowchart of a method for physiological information detection according to another embodiment of the present disclosure. A step S210 of FIG. 4 may be performed between the step S130 and the step S140 of FIG. 1A, or may be incorporated into the step S150 of FIG. 1A.

In the step S210, the processor 110 sets an initial value of the parameter n as 1.

In the step S220, the processor 110 determines whether or not the pulse value ranges between 40 bpm (beats per minute) and 240 bpm according to the pulse-pulse interval P41 of FIG. 3C. If yes, it means the organism 10 is in a stable status. If not, it is possible for the organism 10 to be in an unstable status (for example, in the status after taking exercises); at this time, the measured physiological information is not reliable for the organism 10, and therefore the measured physiological information can be ignored. That is, the signal of such cardiac pulse can be ignored. In addition, the aforementioned "pulse value" is, for example, the number of pulses per minute converted from the pulse-pulse interval P41 of FIG. 3F.

Figure 5:
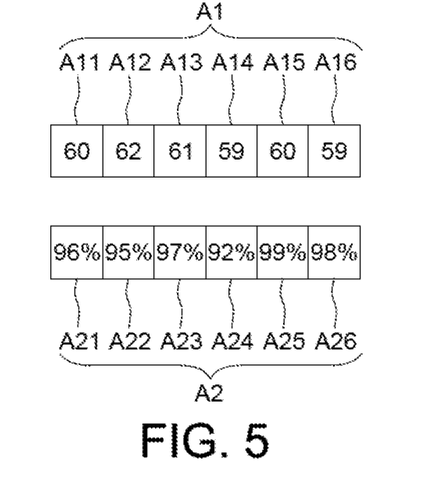
FIG. 5 illustrates a diagram of a physiological message value field according to an embodiment of the present disclosure.

In the step S230, the processor 110 records the current pulse value in the $n^{th}$ pulse value field (which belongs to a physiological information field). FIG. 5 illustrates a diagram of the physiological message value field according to an embodiment of the present disclosure. In FIG. 5, pulse value fields A11-A16 are illustrated. The pulse value fields A11-A16 are the first field (n=1), the second field (n=2), the third field (n=3), the fourth field (n=4), the fifth field (n=5) and the sixth field (n=6), respectively. In the embodiment, the number of the pulse value fields A1 is six, for example. The number of the pulse value fields A1 can also be less or more than six. In addition, the pulse value fields A1 may be an address array of a memory integrated into the processor 110 or independent of the processor 110.

In the step S240, the processor 110 calculates a current physiological message value, for example, blood oxygen saturation according to the first baseline value DC1 and the first amplitude value PA1 of each cardiac pulse of the first physiological signal P1 and the second baseline value DC2 and the second amplitude value PA2 of each cardiac pulse of the second physiological signal P2.

In the step S250, the processor 110 records the current physiological message value in the $n^{th}$ physiological message value field (belongs to the physiological information field), for example, one of the physiological message value fields A21-A26. The physiological message value fields A21, A22, A23, A24, A25 and A26 are the first field (n=1), the second field (n=2), the third field (n=3), the fourth field (n=4), the fifth field (n=5) and the sixth field (n=6) respectively, as illustrated in FIG. 5. The number of the physiological message value fields A2 is six, for example. The number of the physiological message value fields A2 can also be less or more than six. In addition, the physiological message value fields A2 may be an address array of a memory integrated into the processor 110 or independent of the processor 110.

In the step S260, the processor 110 determines whether or not the parameter n is equal to M, wherein M is, for example, the number of the pulse value fields A1 and the number of the physiological message value fields A2, for example, six. When the parameter n is equal to M, it means the pulse value fields A1 and the physiological message value fields A2 are filled up, and the processor 110 proceeds to perform the step S270.

In the step S270, the processor 110 calculates a median (for example, a physiological message reliable value belongs to the physiological information reliable value) of the M physiological message values stored in the M physiological message value fields A2 and a median (for example, a pulse reliable value which belongs to the physiological information reliable value) of the M pulse values stored in M pulse value fields A1. When the parameter n is not equal to M, it means the fields has not been filled up yet, the processor 110 proceeds to perform the step S220 to continue calculating the pulse value and the physiological message value of next cardiac pulse, and stores the pulse value and the physiological message value in next (n=n+1) pulse value field A1 and next (n=n+1) physiological message value field A2 until the parameter n is equal to M. In another embodiment, the physiological information reliable value is, for example, mode of the physiological information or one of the physiological information which is closest to a standard deviation of the physiological information; but the scope of the present disclosure is not limited thereto.

As illustrated in FIG. 5, the M pulse values in the M pulse value fields A1 are 60, 62, 61, 59, 60 and 59, respectively, and the median of the M pulse values is 60. The M physiological message values in the M physiological message value fields A2 are 96%, 95%, 97%, 92%, 99% and 98%, respectively, and the median of the M physiological message values may be obtained by a similar calculation way for the median of the pulse values.

In the step S280, the processor 110 calculates a pulse average of the M pulse values stored in the M pulse value fields A1 and a physiological message average of the M physiological message values stored in the M physiological message value fields A2.

In the step S290, the processor 110 controls the display screen 160 to display the pulse average and the physiological message average. In another embodiment, the step S290 may be omitted.

In yet another embodiment, the pulse value fields A11-A16 of FIG. 5 may be filled with system default values. For example, the pulse value fields A11-A16 may be filled with identical or different values which may be between 60 and 80. Similarly, the physiological message value fields A21-A26 of FIG. 5 may be filled with system default values. For example, the physiological message value fields A21-A26 may be filled with identical or different values which may be between 90% and 99%. Under this situation, the operating flows of FIG. 4 may be omitted.

Figure 6A:
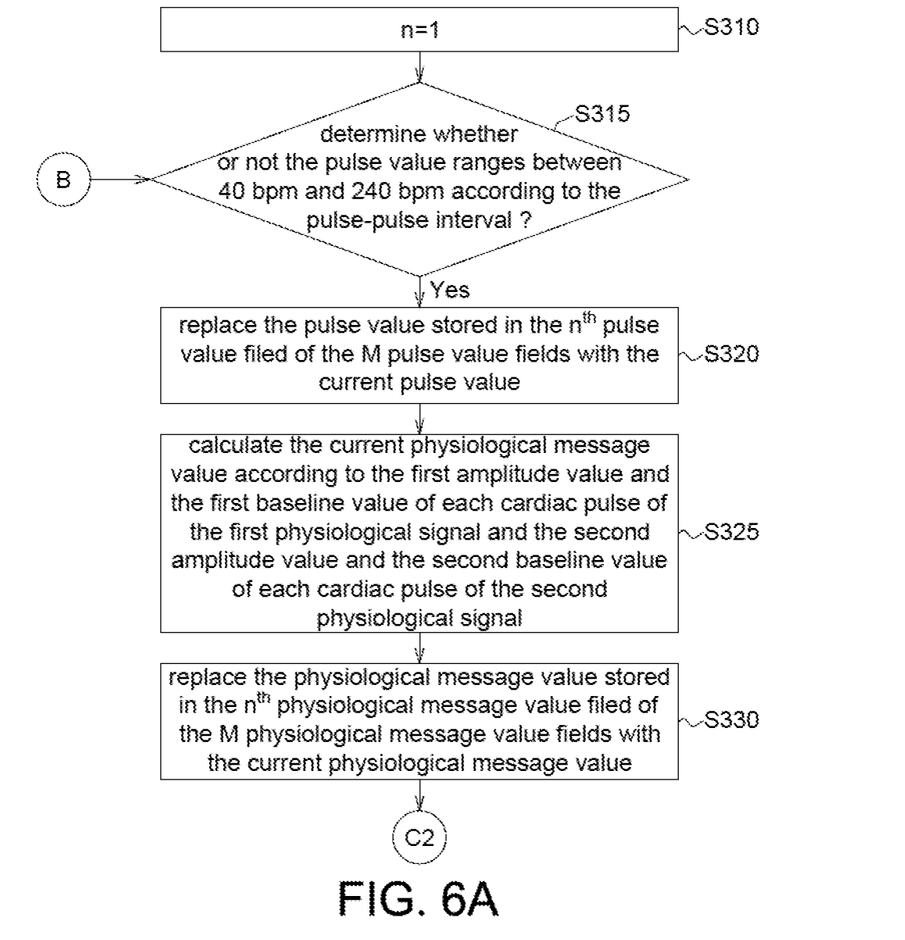
FIGS. 6A and 6B illustrate a flowchart of a detecting method for physiological information according to yet another embodiment of the present disclosure.
Figure 6B:
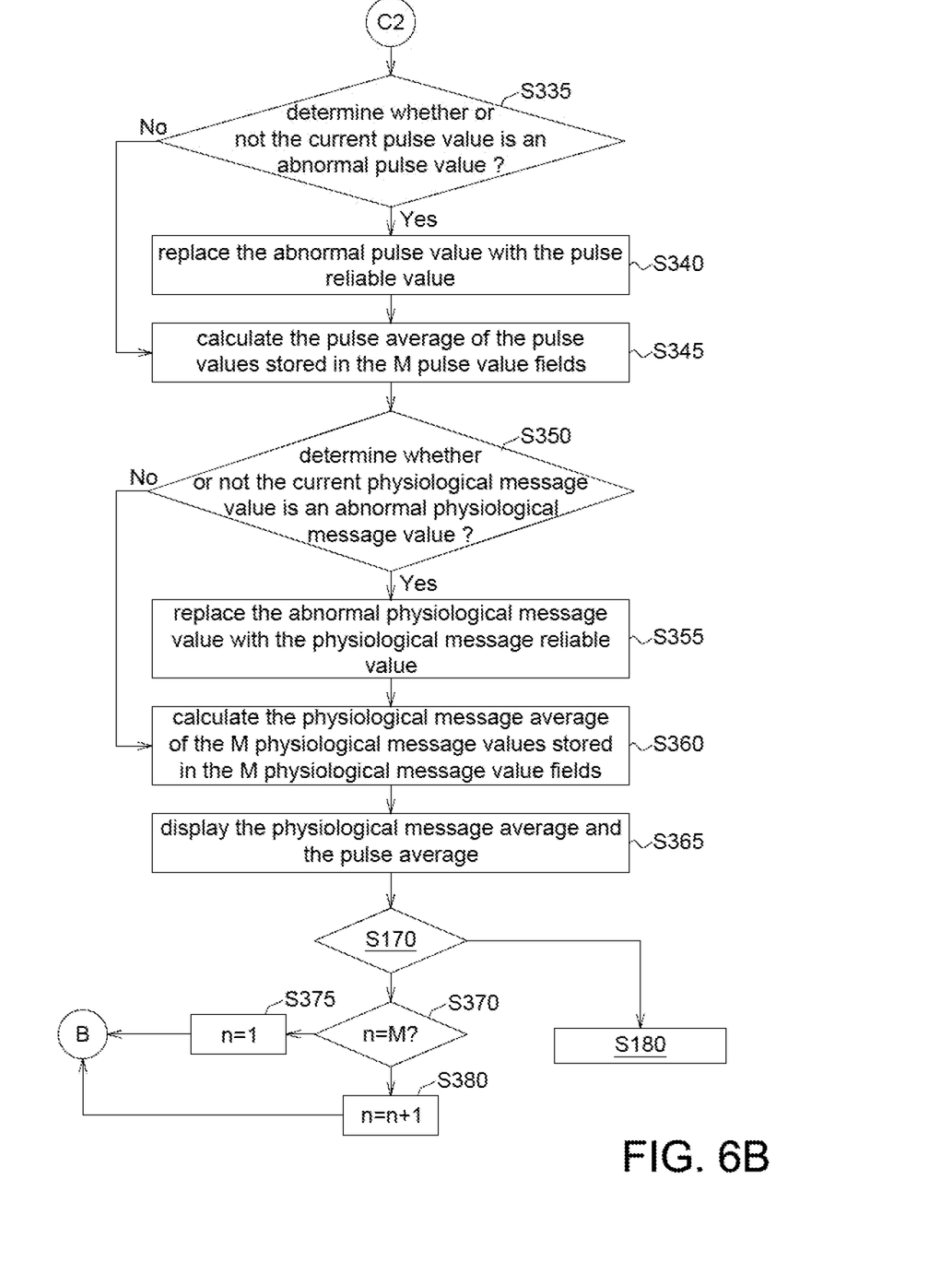

FIGS. 6A and 6B illustrate a flowchart of a detecting method for physiological information according to another embodiment of the present disclosure. Wherein, the step S290 in FIG. 4 may be followed by the step S310 in FIG. 6.

In the step S310, the processor 110 sets the initial value of the parameter n as 1.

Then, the processor 110 performs the step S150 to calculate the first baseline value DC1 and the first amplitude value PA1 of the received cardiac pulse of the first physiological signal P1 and the second amplitude value PA2 and the second baseline value DC2 of the received cardiac pulse of the second physiological signal P2 by using the aforementioned operating flows shown in FIGS. 3A-3F, and then the processor 110 proceeds to perform the step 315.

In the step S315, the processor 110 determines whether or not the pulse value is between 40 bpm and 240 bpm according to the pulse-pulse interval P41 (illustrated in FIG. 3F). If yes, it means that the organism 10 is in a stable status, and then the processor 110 proceeds to perform the follow-up physiological information detection. If not, it means that the organism 10 may be in an unstable status (for example, in the state after taking exercise). At this time, the physiological information is not reliable for the organism 10, and therefore the measured physiological information can be ignored. That is, the signal of this cardiac pulse may be ignored, and the processor 110 goes back to perform the step S150 and further performs the step S315.

Figure 7:
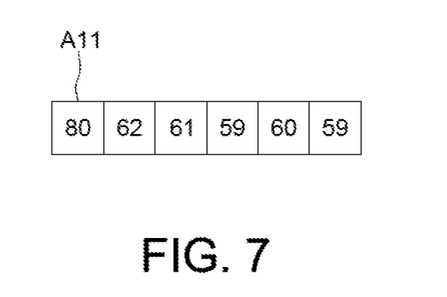
FIG. 7 illustrates a diagram of updated pulse value fields of FIG. 5.

In the step S320, the processor 110 replaces the pulse value stored in the $n^{th}$ pulse value filed of the M pulse value fields A1 with the current pulse value for updating the pulse value fields A1 by the newest pulse value sequentially. FIG. 7 illustrates a diagram of the updated pulse value fields A1 of FIG. 5. As illustrated in FIG. 7, for the current parameter n (n=1), the pulse value of the first pulse value field A11 may be replaced with the current pulse value (for example, 80).

In the step S325, the processor 110 calculates the current physiological message value of the organism 10 according to the first amplitude value PA1 and the first baseline value DC1 of each cardiac pulse of the first physiological signal P1, and the second amplitude value PA2 and the second baseline value DC2 of each cardiac pulse of the second physiological signal P2. The current physiological message value is, for example, blood oxygen saturation.

In the step S330, the processor 110 replaces the physiological message value stored in the $n^{th}$ physiological message value filed of the M physiological message value fields A2 with the current physiological message value for updating the physiological message value fields A2 by the newest physiological message value sequentially. The updating method for the physiological message value fields A2 is similar to that for the pulse value fields A1 of FIG. 7, and therefore the physiological message value fields A2 are not illustrated in FIG. 7.

Figure 8:
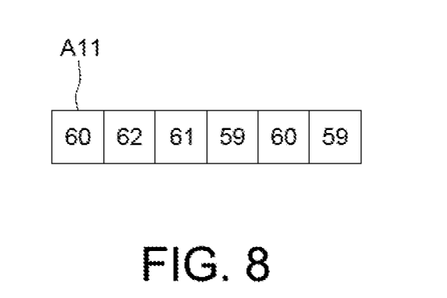
FIG. 8 illustrates a diagram of replacing the abnormal pulse value of FIG. 7.

In step S335, the processor 110 determines whether or not the current pulse value (that is, the pulse value of the $n^{th}$ pulse value field A1) is an abnormal pulse value. If yes, the processor 110 proceeds to perform the step S340 to remove the abnormal pulse value and replaces the abnormal pulse value with the pulse reliable value calculated in the step S270 of FIG. 4. FIG. 8 illustrates an exemplary diagram of replacing the abnormal pulse value of FIG. 7. In the example of the current parameter n being equal to 1, the pulse value (80) of the first pulse value field A11 is replaced with the pulse reliable value (for example, 60). When the current pulse value is a normal pulse value, the processor 110 proceeds to perform the step S345. In the step S345, the processor 110 calculates the average of the pulse values stored in the M pulse value fields A1. In addition, the processor 110 recalculates the pulse reliable value (for example, the M pulse values shown in FIG. 8) of the updated M pulse values stored in the M pulse value fields A1 and replaces the original pulse reliable value with the new pulse reliable value.

Then, in the step S350, the processor 110 determines whether or not the current physiological message value (that is, the physiological message value in the $n^{th}$ physiological message value field A2) is an abnormal physiological message value. If yes, the processor 110 proceeds to perform the step S355 to remove the abnormal physiological message value and replaces the abnormal physiological message value with the physiological message reliable value calculated in the step S270 of FIG. 4. The replacing to method for the abnormal physiological message value may be similar to that for the pulse value fields A1 of FIG. 8, and therefore it is not illustrated in FIG. 8. When the current physiological message value is a normal physiological message value, the processor 110 proceeds to perform the step S360. In the step S360, the processor 110 calculates a physiological message average of the M physiological message values stored in the M physiological message value fields A2. In addition, the processor 110 recalculates the physiological message reliable value of the updated M physiological message values stored in the M physiological message value fields A2 and replaces the original physiological message reliable value with the new physiological message reliable value.

In other words, the processor 110 may be configured to recalculate a new physiological information reliable value for normal physiological information values (that is, the updated physiological information values) and the original physiological information reliable value thereof, and replace the original physiological information reliable value with the new physiological information reliable value.

Then, in the step S365, the processor 110 controls the display screen 160 to display the physiological message average and the pulse average. Since the abnormal pulse value and the abnormal physiological message value have been removed, the displayed physiological message average and the displayed pulse average are significant values (for example, non-distorted value or normal value).

After the step S365, the processor 110 proceeds to perform the step S170. The step S170 has been described above, and it is not repeated here. Then, in the step 370, the processor 110 determines whether or not the parameter n is equal to M. When the parameter n is equal to M, it means the last field (that is, the $M^{th}$ field) has been updated and thus the processor 110 proceeds to perform the step S375. In the step S375, the processor 110 resets the value of the parameter n as 1 and then the proceeds to perform the step S315. When the parameter n is not equal to M, it means the last field (that is, the $M^{th}$ field) has not been updated yet and thus the processor 110 proceeds to perform the step S380. In the step S380, the processor 110 increases the value of the parameter n and proceeds to perform the step S315 to process the next (n=n+1) cardiac pulses of the first physiological signal P1 and the next (n=n+1) cardiac pulses of the second physiological signal P2. It can be understood that the detecting apparatus of the disclosed embodiments stores the newest physiological information in a fixed number of the physiological information fields (such as a fixed number of memory addresses), and therefore the memory capacity for storing the continuously produced physiological information is reduced.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A detecting apparatus for physiological information, comprising:
   a first optical signal provider configured to provide an organism with a first optical signal, wherein the first optical signal after interacting with the organism turns into a first physiological signal;
   a signal receiver configured to receive the first physiological signal during a period of time; and
   a processor, configured to calculate a plurality of physiological information of the organism according to the first physiological signal, determine whether or not there is an abnormal physiological information value of the physiological information values, and replace the abnormal physiological information value with a physiological information reliable value based on normal physiological information values of the plurality of physiological information values when there is the abnormal physiological information value;
   wherein the abnormal physiological information value is a distorted measurement signal, and the normal physiological information value is a non-distorted signal;

wherein the detecting apparatus further comprises:
a second optical signal provider, configured to provide the organism with a second optical signal, wherein the second optical signal after interacting with the organism turns into a second physiological signal;
wherein the signal receiver is further configured to receive the second physiological signal;
the processor is further configured to:
calculate the plurality of physiological information values of the organism according to the first physiological signal and the second physiological signal;
synthesize the first physiological signal and the second physiological signal to form a synthetic physiological signal;
differentiate the synthetic physiological signal once to obtain a differential curve;
determine a maximum value of the differential curve;
obtain a first amplitude value of the first physiological signal;
obtain a second amplitude value of the second physiological signal;
determine a corresponding point on the differential curve, wherein the corresponding point is most adjacent to the maximum value of the differential curve and the corresponding point equals or approximates to zero;
obtain a first baseline value of the first physiological signal corresponding to the corresponding point, wherein the first baseline value is wave trough of the first physiological signal;
obtain a second baseline value of the second physiological signal corresponding to the corresponding point, wherein the second baseline value is wave trough of the second physiological signal;
obtain a first index default value and a second index default value according to the maximum value of the differential curve, wherein the first index default value is defined as a ratio of the first amplitude value to the first baseline value, and the second index default value is defined as a ratio of the second amplitude value to the second baseline value;
determine whether or not a first blood perfusion index (PI) of each of a plurality of cardiac pulses of the first physiological signal reaches the first index default value and a second blood perfusion index of each of a plurality of cardiac pulses of the second physiological signal reaches the second index default value;
output an alarm signal when each first blood perfusion index does not reach the first index default value and each second blood perfusion index does not reach the second index default value.

2. The detecting apparatus according to claim 1, wherein the processor is further configured to calculate a physiological information average, for the physiological information reliable value and the normal physiological information values.

3. The detecting apparatus according to claim 2, further comprising:
a display screen configured to display the physiological information average.

4. The apparatus according to claim 2, wherein the processor is configured to recalculate a new physiological information reliable value for said normal physiological information values and said physiological information reliable value thereof, and replace the physiological information reliable value with the new physiological information reliable value.

5. The detecting apparatus according to claim 1, further comprising:
a memory having a plurality of physiological information fields for storing the plurality of physiological information values.

6. The detecting apparatus according to claim 1, wherein the detecting apparatus further comprises an indicator, and the processor is further configured to:
adjust a driving parameter of the first optical signal provider, such that the first baseline value of the plurality of cardiac pulses of the first physiological signal reaches a first baseline default value;
set the first baseline value and the first amplitude value of the first physiological signal as a first baseline initial value and a first amplitude initial value, respectively, when the first blood perfusion index reaches the first index default value;
continuously calculate the first baseline value and the first amplitude value of each cardiac pulse of the first physiological signal;
continuously determine whether or not the first baseline value and the first amplitude value of each cardiac pulse of the first physiological signal deviate from the first baseline initial value and the first amplitude initial value, respectively, within a time interval; and
control the indicator to output the alarm signal when the first baseline value and the first amplitude value of the cardiac pulse of the first physiological signal deviate from the first baseline initial value and the first amplitude initial value, respectively, within the time interval.

7. The detecting apparatus according to claim 1, wherein the physiological information reliable value is chosen from a group consisting of a mode of the plurality of physiological information values, a median of the plurality of physiological information values, and one of the plurality of physiological information values which is closest to a standard deviation of the plurality of physiological information values.

8. A detecting method for physiological information, comprising:
providing a detecting apparatus having a first optical signal provider, a signal receiver, and a processor;
providing an organism with a first optical signal by the first optical signal provider, wherein the first optical signal after interacting with the organism turns into a first physiological signal;
receiving, the first physiological signal by the signal receiver;
calculating, by the processor, a plurality of physiological information values of the organism according to the first physiological signal;
determining, by the processor, whether or not there is an abnormal physiological information value of the physiological information values; and
replacing, by the processor, the abnormal physiological information value with a physiological information reliable value based on normal physiological information values of the plurality of physiological information values when there is the abnormal physiological information;
wherein the abnormal physiological information value is a distorted measurement signal, and the normal physiological information value is a non-distorted signal;
wherein the detecting method further comprises:
providing, by a second optical signal provider, the organism with a second optical signal, wherein the second optical signal after interacting with the organism turns into a second physiological signal;

receiving, by the signal receiver, the second physiological signal;

calculating, by the processor, the plurality of physiological information values of the organism according to the first physiological signal and the second physiological signal;

synthesizing the first physiological signal and the second physiological signal to form a synthetic physiological signal;

differentiating the synthetic physiological signal once to obtain a differential curve;

determining a maximum value of the differential curve;

obtaining a first amplitude value of the first physiological signal;

obtaining a second amplitude value of the second physiological signal;

determining a corresponding point on the differential curve, wherein the corresponding point is most adjacent to the maximum value of the differential curve and the corresponding point equals or approximates to zero;

obtaining a first baseline value of the first physiological signal corresponding to the corresponding point, wherein the first baseline value is wave trough of the first physiological signal;

obtaining a second baseline value of the second physiological signal corresponding to the corresponding point, wherein the second baseline value is wave trough of the second physiological signal;

obtaining a first index default value and a second index default value according to the maximum value of the differential curve, wherein the first index default value is defined as a ratio of the first amplitude value to the first baseline value, and the second index default value is defined as a ratio of the second amplitude value to the second baseline value;

determining whether or not a first blood perfusion index of each of a plurality of cardiac pulses of the first physiological signal reaches the first index default value and a second blood perfusion index of each of a plurality of cardiac pulses of the second physiological signal reaches the second index default value; and outputting an alarm signal when each first blood perfusion index does not reach the first index default value and each second blood perfusion index does not reach the second index default value.

9. The detecting method according to claim 8, further comprises:

calculating, by the processor, a physiological information average, for the physiological information reliable value and the normal physiological information values.

10. The detecting method according to claim 9, further comprises:

displaying the physiological information average.

11. The detecting method according to claim 9, further comprising:

recalculating, by the processor, a new physiological information reliable value for said normal physiological information values and said physiological information reliable value thereof; and replacing, by the processor, the physiological information reliable value with said new physiological information reliable value.

12. The detecting method according to claim 8, wherein the detecting apparatus further comprises a memory having a plurality of physiological information fields for storing the plurality of physiological information values.

13. The detecting method according to claim 8, further comprises:

adjusting a driving parameter of the of the first optical signal provider, such that the first baseline value of the first physiological signal reaches a first baseline default value;

setting the first baseline value and the first amplitude value of the first physiological signal as a first baseline initial value and a first amplitude initial value, respectively, when the first blood perfusion index reaches the first index default value;

continuously calculating a first baseline value and a first amplitude value of each cardiac pulse of the first physiological signal;

continuously determining whether or not the first baseline value and the first amplitude value of the cardiac pulse of the first physiological signal deviate from the first baseline initial value and the first amplitude initial value, respectively, within a time interval; and controlling an indicator to output the alarm signal when the first baseline value and the first amplitude value of the cardiac pulse of the first physiological signal deviate from the first baseline initial value and the first amplitude initial value, respectively, within the time interval.

14. The detecting method according to claim 8, wherein the physiological information reliable value is chosen from a group consisting of a mode of the plurality of physiological information values, a median of the plurality of physiological information values, and one of the plurality of physiological information values which is closest to a standard deviation of the plurality of physiological information values.

15. The detecting method according to claim 1, wherein the first optical signal provider is red light emitter, and the second optical signal provider is an Infrared light emitter.

* * * * *